United States Patent
Lombardy, Jr. et al.

(10) Patent No.: US 6,235,318 B1
(45) Date of Patent: *May 22, 2001

(54) EFFERVESCENT CHEWING GUM

(75) Inventors: Charles M. Lombardy, Jr., 13395 Ledgebrook La; David R. Lombardy, 97 Olive St., both of Chagrin Falls, OH (US) 44022; Jeffrey Wayne Liebrecht, Columbus, OH (US)

(73) Assignees: Charles M. Lombardy, Jr.; David R. Lombardy, both of Chagrin Falls, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/234,815

(22) Filed: Jan. 21, 1999

(51) Int. Cl.$^7$ ................. A23G 3/30; A61K 9/68
(52) U.S. Cl. ................. 426/3; 424/48; 424/440; 426/5
(58) Field of Search ............... 426/3, 5; 424/48, 424/440

(56) References Cited

U.S. PATENT DOCUMENTS

| | | |
|---|---|---|
| 2,470,906 | 5/1949 | Taylor . |
| 3,431,339 | 3/1969 | Gyarmathy et al. ............ 424/52 |
| 3,518,345 | 6/1970 | Dines et al. ............ 424/44 |
| 3,622,352 * | 11/1971 | Daylor ............ 426/5 |
| 3,888,976 | 6/1975 | Mlkvy et al. ............ 424/44 |
| 3,946,108 | 3/1976 | Tomlison et al. ............ 424/49 |
| 3,962,417 | 6/1976 | Howell ............ 424/52 |
| 4,156,740 | 5/1979 | Glass et al. ............ 426/3 |
| 4,169,885 | 10/1979 | Raaf et al. ............ 424/16 |
| 4,260,596 | 4/1981 | Mackles ............ 424/14 |
| 4,289,794 | 9/1981 | Kleiner et al. ............ 426/660 |
| 4,301,178 | 11/1981 | Witzel et al. ............ 426/5 |
| 4,316,915 | 2/1982 | Friello et al. ............ 426/5 |
| 4,466,983 | 8/1984 | Cifrese et al. ............ 426/5 |
| 4,513,012 | 4/1985 | Carroll et al. ............ 426/5 |
| 4,537,764 | 8/1985 | Pellico et al. ............ 424/50 |
| 4,563,345 | 1/1986 | Arrick ............ 424/48 |
| 4,568,537 * | 2/1986 | Hoerman ............ 426/5 X |
| 4,581,234 | 4/1986 | Cherukuri et al. ............ 426/3 |
| 4,639,368 * | 1/1987 | Niazi et al. ............ 426/3 |
| 4,683,138 | 7/1987 | Glass et al. ............ 426/5 |
| 4,698,223 | 10/1987 | Perfetti et al. ............ 426/4 |
| 4,753,792 | 6/1988 | Aberg ............ 424/44 |
| 4,975,288 | 12/1990 | Hager et al. ............ 426/5 |
| 4,980,178 | 12/1990 | Cherukuri et al. ............ 426/5 |
| 4,983,379 | 1/1991 | Schaeffer ............ 424/52 |
| 5,008,106 | 4/1991 | Merianos et al. ............ 424/80 |
| 5,059,428 * | 10/1991 | Wong et al. ............ 426/3 |
| 5,125,819 | 6/1992 | Hager et al. ............ 425/133.1 |
| 5,139,797 | 8/1992 | Huzinec et al. ............ 426/3 |
| 5,380,530 | 1/1995 | Hill ............ 424/440 |
| 5,607,681 | 3/1997 | Galley et al. ............ 424/52 |
| 5,618,517 * | 4/1997 | Miskewitz ............ 426/5 X |
| 5,629,035 * | 5/1997 | Miskewitz ............ 426/5 |
| 5,693,334 * | 12/1997 | Miskewitz ............ 426/5 X |
| 5,698,215 | 12/1997 | Kalili et al. ............ 424/440 |
| 5,709,873 | 1/1998 | Bar-Shalom et al. ............ 424/422 |
| 5,789,002 * | 8/1998 | Duggan et al. ............ 426/5 X |
| 5,824,291 * | 10/1998 | Howard ............ 424/48 |

FOREIGN PATENT DOCUMENTS

| | | |
|---|---|---|
| 2112642 | 12/1982 | (GB) . |
| 91/07184 | 5/1991 | (WO) . |
| 97/04662 * | 2/1997 | (WO) ............ 426/5 |
| 97/19668 | 6/1997 | (WO) . |

OTHER PUBLICATIONS

Machperson, An in Vitro Simulation of the Effects of Chewing Sugar–Free and Sugar–Containing Chewing Gums on PH Changes in Dental Plaque, J Dent Res Oct. 1993;72(10):1391–1397.

Loos et al., A New Candy that Prevent Cavities, www.smiledoc.com/dentist/candy.html Oct. 11, 1998.

Vigoren, The World's First Toothbrush in a Tablet, Yow! Laboratories, Inc.

* cited by examiner

*Primary Examiner*—Arthur L. Corbin
(74) *Attorney, Agent, or Firm*—Standley & Gilcres LLP

(57) ABSTRACT

Disclosed is an oral hygiene preparation which is plaque disrupting in the form of a chewing gum. The chewing gum comprises a core containing a carbonate and/or bicarbonate which is surrounded by a coating that contains an encapsulated edible acid. Upon mastication the chewing gum effervesces, thus promoting the cleansing and breath freshening properties of the preparation.

20 Claims, No Drawings

EFFERVESCENT CHEWING GUM

TECHNICAL FIELD

The present invention relates to a novel chewing gum which, when chewed, fights plaque, invigorates the tissue surrounding the necks of the teeth, reduces cavities in teeth, whitens and polishes teeth, and freshens breath. The inventive chewing gum, in a preferred embodiment, comprises a sodium bicarbonate gum base encapsulated with a citric acid coating.

BACKGROUND OF THE INVENTION

Adhesion of oral bacteria to hard surfaces in the oral cavity (restorations, enamel and cement) is one of the main events leading to the development of oral diseases. Adhesion of bacteria to tooth surfaces results in the formation of dental plaque. Dental plaque leads to tooth decay, calculus, gingivitis and periodontitis. Bacterial adherence to dental surfaces can be facilitated by several mechanisms. It is clear that eliminating bacterial deposition on hard surfaces in the oral cavity is a major step in combating oral diseases. The ability of chemical agents to remove plaque is limited. To date, there has been no good alternative to the mechanical removal of plaque through brushing and flossing.

Conventional chewing gum is a mixture of natural or synthetic gums and resins, sweetened with sugar, corn syrup, artificial sweeteners and may also contain coloring agents and flavor. It is a uniquely U.S. product, discovered during the search for rubber materials in the 1860's. The first manufacturing patent for chewing gum was issued in 1869.

The basic raw material for all chewing gum is the natural gum chicle, obtained from the sapodilla tree indigenous to Central America. Because chicle is relatively expensive and often difficult to procure, other natural gums are also used. Recently, synthetic materials such as polyvinylacetate and similar polymers have come into widespread use.

The chewing gum manufacturer melts, washes and filters the crude gum to remove all foreign materials. The gum is then blended with other natural and synthetic resins, waxes and plasticizers, which are added to control the stickiness and chewing characteristics, and the compound is heated, mixed until uniform, cooled and blocked. The blocked gum base is then stored until needed.

The manufacturer of chewing gum starts with a mix of about 22–25% gum base, about 50–60% powdered sugar, about 12–20% corn syrup and about 1–2% color and flavors. This mixture is heated to about 80° C., thoroughly blended, cooled, extruded onto a belt, rolled to proper thickness, then cut, wrapped and packaged. Bubble gum differs from ordinary gum only in that its base is formulated with rubber latex for greater strength.

Sugarcoated gum is made by whirling small cubes of gum in copper pans with sugar syrup, powdered sugar, color and flavor. This mixture builds the colorful, polished, crystallized sugar shell. Sugarless gums are made by substituting sugar alcohols (xylitol, mannitol or sorbitol) for ordinary sugar.

The chewing of gum is very common among both adults and young people. Chewing gum can serve as a drug delivery system, may contain sugar substitutes which are not cariogenic, and may even serve as an anti-bacterial agent. Chewing gum also induces salivary flow which aids in the cleansing of bacteria from the oral cavity. The present invention proposes using a unique form of chewing gum wherein the inventive effervescent gum possesses unique properties that will reduce plaque and freshen the breath.

BACKGROUND ART

Liquid or gel center-filled products, such as Freshen-up Gum (sugar) and Chewels (sugar-free), both manufactured by Warner-Lambert, are currently on the market and are related to the present invention in texture and mouthfeel. However, these gums do not have decay preventive properties, plaque fighting ability or effervescence as found in the present invention. Another product presently on the market is "Yow!" produced by Yow! Laboratories of Fountain Valley, Calif. It is described as a sugar free, bubbling formula that helps reduce plaque and eliminate bad breath. This product is not a chewing gum oral hygiene product.

U.S. Pat. No. 2,470,906 to Taylor discloses a dentifrice containing ascorbic acid and acid analogues of ascorbic acid. The patent describes the use of ascorbic acid to transform mucinous coatings in the oral cavity into easily removable forms. The Taylor dentifrice is also disclosed as containing calcium diphosphate, potassium-aluminum silicate, and flavors. There is no suggestion of a chewing gum dentifrice nor of effervescence.

U.S. Pat. No. No. 3,431,339 to Gyarmathy et al. discloses a chewable dental tablet to be used in conjunction with a toothbrush. The tablet is disclosed as containing a polishing agent, flourine—containing agents, a foaming agent and a waxy releasable matrix.

U.S. Pat. No. 3,962,417 to Howell discloses an effervescent dentifrice in chewable tablet form that is effective against *Bacillus acidophilios*. The Howell dentifrice tablet was prepared by dry-mixing sodium lauryl sulphate, saccharin, chlorophyllin, magnesium carbonate, citric acid, calcium carbonate, sodium bicarbonate, flavors, magnesium stearate, acacia powder and stannous fluoride. This patent does not disclose nor suggest an oral hygiene chewing gum that comprises a gum stock and a coating containing an edible acid.

U.S. Pat. No. 4,127,645 to Witzel et al. discloses an effervescent tablet that comprises a core portion containing an effervescent couple, and an outer portion which coats or surrounds the core portion. The outer portion is taught to contain a sugar alcohol, such as sorbitol. There is no suggestion of an effervescent chewing gum wherein the base containing gum stock is covered with an acid containing coating.

U.S. Pat. No. 4,169,885 to Raaf et al. discloses a dental hygiene product in the form of a capsule or a filled sweet comprising an outer shell of a hydrophilic substance containing a therapeutic substance such as a fluoride compound and an inner filling material comprising a hydrophobic material such as fats and waxes. This patent teaches that the therapeutic compound is released while the outer shell is dissolved in the mouth. Upon reaching the inner core, the wax or fat coats the teeth thereby retaining the therapeutic in contract with the teeth and gums. This patent makes no mention or suggestion of an effervescent chewing gum.

U.S. Pat. No. 4,563,345 to Arrick discloses a chewing gum having a first phase comprising a chewable material, and a second viscous phase including a fluoride compound.

U.S. Pat. No. 4,753,792 to Aberg discloses a water free, non-oil based, tooth cleaning tablet. The tablet is disclosed as being self-foaming when chewed in the mouth. The tablet is disclosed to comprise less than 50% by weight of a self foaming effervescent couple (i.e. sodium bicarbonate and acid), greater than 35% by weight of an insoluble filling and polishing composition, and an effective amount of a fluoride tooth protecting agent. The Aberg tablet, upon chewing, forms a paste. There is no suggestion of using a chewing gum or separating the effervescent base from the acid.

U.S. Pat. No. 5,380,530 to Hill discloses a therapeutic chewing gum wherein the chewing gum is coated with an emulsion comprising an ingestible surfactant—emulsifier and a polydimethyl siloxane insoluble in said surfactant emulsifier. The coating is taught to contain anti-microbials, stannous fluoride, antioxidants, enzymes, antibiotics, analgesics and others. There is no suggestion in this patent to place an encapsulated edible acid in the coating which surrounds a gum stock that comprises a base, so that upon mastication, an effervescent reaction occurs.

U.S. Pat. No. 5,698,215 to Kalili et al. describes a chewing gum composition with fluoride and citric acid. The patentees propose that their chewing gum utilizes a biochemical reaction which takes place when dental enamel is exposed to citric acid. It is suggested that citric acid opens pores in the dental enamel which allows fluoride to penetrate the prismatic layers of the tooth structure. This patent makes no reference to an effervescent chewing gum wherein the citric acid is encapsulated and is found in the coating portion of the chewing gum piece.

PCT/MX96/00019 patent application (WO97/19668) to Cristiani-Garcia et al. discloses a toothpaste and mouthwash in tablet form which dissolves in the mouth when contacting the saliva. Each tablet is described as containing ascorbic acid 18 mg, sodium bicarbonate 50 mg, tricalcic phosphate 40 mg, sodium laurilsulfate 17 mg, arabic gum 70 mg and natural sweetness and flavoring agents 150 mg. This reference does not disclose nor suggest the use of a chewing gum and further, it fails to suggest that the ascorbic acid be placed in microcapsules and then incorporated into a coating which surrounds a gum stock.

It is thus apparent that a need exists for a sugar-free, effervescent chewing gum that will prevent dental plaque and freshen breath while allowing an inexpensive, convenient method of improving oral hygiene without causing undesired changes of the oral micro flora.

SUMMARY OF THE INVENTION

In general, the present invention is directed to a solid chewable piece of chewing gum comprising:
  a) a chewing gum base wherein said base comprises at least one component selected from the group consisting of: alkali metal carbonates, alkali metal bicarbonates, alkaline earth metal carbonates, alkaline earth metal bicarbonates and mixtures thereof; and
  b) a coating covering said base wherein said coating comprises at least one edible acid.

The pH of the chewing gum during the initial mastication will be less than about 4.0 to induce salivary flow immediately, and upon further mastication during the stage of effervescence and thereafter the pH is about 7.0 and above. This feature is important as it has been reported that the oral pH should be about 5.5 to counteract the acids produced by bacteria. In one embodiment of the invention the preferred pH of the chewing gum after effervescence is 7.3 and higher. The chewing gum is designed to create an initial blast of tartness that will induce salivary flow. The saliva produced should be retained in the mouth and used like a mouthwash to swish back and forth between the teeth for at least 15 seconds. This action allows the foaming action to penetrate all the crevices of the teeth and gums, loosening food particles and plaque. The user then continues chewing for at least 15 minutes for additional tooth polishing and long lasting breath freshening. The consumers teeth will have a squeaky clean feeling and the tissues of the oral cavity will be invigorated.

In a more preferred embodiment, the piece of chewing gum additionally comprises at least one component selected from sweeteners, therapeutic agents, flavoring ingredients, processing aids, edible oils and breath fresheners. In a further embodiment, the edible acid is encapsulated prior to its inclusion in the coating.

In a more specific embodiment, this invention relates to a sugar-free, effervescent chewing gum comprising:
  1) a chewing gum base formulation comprising:
    a) sodium bicarbonate;
    b) xylitol (a natural sweetener);
    c) mannitol (a bulking agent, humectant and sweetener for a cooling sensation);
    d) aspartame and acesulfame K (artificial sweeteners);
    e) at least one oil selected from the group consisting of: parsley seed oil (a breath freshener), eucalyptus oil (antibacterial), thyme oil (antibacterial), and myrrh oil (gum stimulant);
    f) sorbitol (as natural sweetener and bulking agent); and
  2) a coating formulation comprising at least one edible acid.

In a more preferred embodiment, the gum base is coated with a coating comprising an edible acid selected from tartaric acid, citric acid, malic acid, ascorbic acid, acid phosphate salts (i.e. monocalcium phosphate) and mixtures thereof. Especially preferred is encapsulated ascorbic acid and citric acid. The coating may also contain $TiO_2$ as a product whitener.

The effervescent chewing gum, according to the invention, is useful to clean teeth and freshen breath. Further, the novel dental oral hygiene gum utilizes effervescence to enhance a person's ability to prevent gum disease, and polish and whiten teeth.

The oral hygiene gum, according to the invention, is preferably void of agents, such as sweeteners, that would promote tooth decay and/or gum disease. Artificial sweeteners such as aspartame and acesulfame K are preferred. The oral hygiene gum may also contain natural and/or artificial flavors, with natural flavors being preferred. The gum, according to the invention, may also include coloring agents (in addition to the $TiO_2$ or in place of), however, the use of coloring agents is not preferred.

The presence of a base compound in the core gum stock is required. The useful bases include calcium carbonate and sodium bicarbonate. The use of sodium bicarbonate and calcium carbonate is especially preferred as this combination possesses the added feature of being a "tooth polisher" in addition to providing part of the "foaming" component.

The effervescence system (i.e. sodium bicarbonate and citric acid) of the inventive chewing gum comprises from 10 to 50% by weight of the final product. More preferably the effervescence system comprises 10–40% by weight of the final product, with 20–35% by weight being most preferred. Further, the weight ratio of acid to base can range from 0.5 to 2.0 with 0.6 to 1.0 being more preferred and 0.7 to 0.8 being most preferred. This ratio of acid to base is important as the final pH of the chewing gum at the end of mastication should be as high as possible.

There if further disclosed an effervescent solid piece of chewing gum comprising by weight:
  a) 25–35% gum base;
  b) 30–40% of at least one compound selected from Xylitol, mannitol and sorbitol;
  c) 2–10% glycerin;
  d) 0.1–0.5% of at least one oil selected from peppermint, menthol, eucalyptus, parsley, thyme and myrrh;
  e) 0.2–0.5% of at least one artificial sweetener;
  f) 0.5–1.0% lecithin;
  g) 2.0–10% calcium carbonate;

h) 5.0–15% sodium bicarbonate; and i) 5.0–15% of at least one edible acid.

DETAILED DESCRIPTION OF THE INVENTION

One of the major problems associated with the production of an effervescent oral hygiene chewing gum is shelf life. Those skilled in the art will readily appreciate that the organic acids and bases used to generate the effervescent must be kept separate before the time effervescence is desired. While the presence of a liquid, such as water, is required before the reaction will occur, even small levels of moisture found in chewing gum will allow for the reaction to take place over time. With desired shelf-lives of more than one year, an effervescent chewing gum must be stable, while promptly evidencing effervescence once placed in the mouth and chewed. The production of a strong and stable effervescent chewing gum is one aspect of the invention.

In the production of long-shelf lived effervescent chewing gum pieces for oral hygiene in accordance with this invention, the basic components, which are the alkali metal carbonates and/or bicarbonates are dispersed within the chewing gum base which also includes aromatic oils, sweeteners, whiteners and therapeutic agents, to result in a gum stock. The edible acids, such as tartaric, citric, ascorbic, malic, acid phosphate salts or mixtures thereof are found in the coating surrounding the gum stock. The edible acids are preferably encapsulated to prevent their reaction with the carbonates and/or bicarbonates that are present in the base formulation. The coating may also include flavoring agents, sweeteners, therapeutic agents, and coloring agents. Once placed in the mouth, mastication initially dissolves the coating, releasing the acid which promotes further salivation and upon further mastication of the chewing gum piece the reaction (generation of $CO_2$) between the base and the acid begins, thus producing a vigorous effervescence. This vigorous effervescence in combination with the chewing and the various therapeutic agents (i.e. whiteners and breath fresheners) results in a pleasing hygienic experience for the consumer.

The chewing gum piece is designed so that the effervescence continues for at least 1 minutes, more preferably at least 3 minutes, and most preferably at least 5 minutes. It should be noted that the effervescent chewing gum, according to the invention, does not preclude the presence of fluoride. However, it is the inventors' belief that fluoride compounds need not be present in the inventive chewing gum since other fluoride sources such as commercially available toothpaste and fluoridated drinking water provide adequate levels to the consumer. Further, the effervescent chewing gum, according to the invention, is not intended to replace good tooth brushing habits and proper oral hygiene. The purpose of the inventive chewing gum is to supplement a total program of dental care. Prevention is the key to total dental care and visits to a dentist are an important part of the prevention process.

In general, known techniques can be used to produce the chewing gum with plaque fighting capabilities in accordance with the invention. One aspect of this invention resides in the discovery that the sodium bicarbonate gum base coupled with edible acid encapsulation in the coating provides a highly acceptable, non-toxic chewing gum that does not interfere with other oral hygiene regimes. Furthermore, use of such an anti-plaque chewing gum does not eradicate the beneficial bacteria in the oral cavity, thus minimizing undesired changes in the oral microflora.

Experimental

In actual use, the sugarless gum of the present invention would be used by both adults and children as it is a convenient, low cost method of maintaining oral hygiene. The present invention may be better understood in view of the following examples which are illustrative only and should not be construed as limiting the invention.

Preliminary experiments were performed in the development of this invention which were directed to physically admixing various compounds to determine the most effective combinations.

Five (5) experiments were conducted.

1) the Control;

2) Experimental No. 1—the Control plus Essential Oils (parsley seed, myrrh, eucalyptus, and thyme);

3) Experimental No. 2—the mixture of #2 combined with calcium carbonate and a two fold increase in the oil concentration;

4) Experimental No. 3—the mixture of #3 plus sodium carbonate, coated with citric acid (to simulate a pan coated gum); and 5) Experimental No. 4—the mixture of #3 plus sodium bicarbonate mixed in with citric acid.

The Control served as a baseline for evaluating the gum mixing process and the oral hygiene ingredient variables. The oral hygiene formulations were developed taking into account the desired product indications and the intended use attributes (i.e. final pH).

General Process Conditions

The process to prepare the base gum stock included placing the lecithin and the gum base in a heated blender (5 liter Stephan mixer) and the gum base was softened to about 60° C. Dry blending of 95% of the mannitol, sorbitol and xylitol was conducted to prepare Dry Blend No. 1. Dry blending of the aspartame, acesulfame K and flavor enhancers together with the remaining 5% portion of the mannitol, sorbitol and xylitol was conducted to prepare Dry Blend No. 2.

Dry Blend No. 1 was then added to the gum base/lecithin mixture in the Stephan mixer. Mixing continued until the mass was homogeneous. The glycerin and maltitol syrup was then added and mixing continued until homogeneous (about 5 minutes). Dry Blend No. 2 was then added with mixing, followed by flavor oil. Mixing was continued until a homogeneous mass resulted. This is the Control Base Stock. To the Control Base Stock was added the various active ingredients set forth below to prepare Experimental Nos. 1–4.

EXAMPLE I

The following Table 1 lists the compounds and amounts that were mixed in a 5 liter Stephan mixer to prepare the Control product. The ingredients listed in the following Tables were obtained from the following manufacturers:

Gum Base—Cafosa Gum S/A of Madrid, Spain, Prestige PL gum base.

Xylitol Powder—Cultor Food Science of Ardsley, N.Y., CM90 crystalline xylitol.

Mannitol Powder—Roquette, Inc. of Keokuk, Iowa.

Sorbitol Powder—Roquette, Inc. of Keokuk, Iowa, Neosorb P60W sorbitol FCC.

Glycerin—Vitusa Products, Inc. of Berkley Heights, N.J., kosher glycerin USP.

Peppermint/Menthol Flavor Oil—Givaudan Roure, Inc. of Clifton, N.J.

Flavor Enhancer—Flavor and Fragrance Spec. of Mahwak, N.J.

Acesulfame K—Nutrinova, Inc. of Somerset, N.J.

Aspartame—Monsanto of St. Louis, Mo.

Lecithin—Central Soya of Fort Wayne, In. Centrophill K lecithin.

Calcium Carbonate—Watson Foods Co., Inc. of West Haven, Conn., FCC, 1–40 micron.

Sodium bicarbonate—Rhône-Poulenc, Inc. of Cranberry, N.J.

Citric acid (encapsulated)—Balchem, Inc. of Slate Hill, N.Y., 85% citric acid, FCC, USP;

Eucalyptus, Parsley, Thyme and Myrrh Oils—Frutarom Meer Corp. of North Bergen, N.J.

TABLE 1

Control

| % by wt. of Formulation | Ingredient | Batch Quantity gms |
|---|---|---|
| 30.000% | Gum Base | 450.000 |
| 15.000% | Xylitol Powder | 225.000 |
| 5.000% | Mannitol Powder | 75.000 |
| 5.000% | 85% Maltitol Syrup | 75.000 |
| 38.225% | Sorbitol Powder | 573.375 |
| 5.000% | Glycerin | 75.000 |
| 0.750% | Peppermint/Menthol Flavor Oil | 11.250 |
| 0.075% | Flavor Enhancer | 1.125 |
| 0.100% | Aspartame | 1.500 |
| 0.100% | Acesulfame Potassium | 1.500 |
| 0.750% | Lecithin | 11.250 |
| 0.000% | Calcium Carbonate (1–40 microns) | 0.000 |
| 0.000% | Sodium bicarbonate | 0.00 |
| 0.000% | Citric Acid (encapsulated) | 0.00 |
| 0.000% | Eucalyptus Essential Oil | 0.000 |
| 0.000% | Parsley Seed Essential Oil | 0.00 |
| 0.000% | Thyme Essential Oil | 0.000 |
| 0.000% | Myrrh Essential Oil | 0.00 |

The 1500 gms of the resulting gum product produced was divided in pieces of about 3.5 gms each. A sensory evaluation of the gum produced in this example (control) indicated that it had good sweetness, flavor and generally a pleasing mouthfeel. The use of xylitol, a sugar alcohol, is preferred as it is sweet, not absorbed through the intestine and does not promote tooth decay.

EXAMPLE II

The following Table 2 lists the ingredients and amounts mixed in a 5 liter Stephan mixer to prepare Experimental No. 1.

TABLE 2

Experimental No. 1
Control Plus Essential Oils

| % of Formulation | Ingredient | Batch Quantity gms |
|---|---|---|
| 30.000% | Gum Base | 450.000 |
| 15.000% | Xylitol Powder | 225.000 |
| 5.000% | Mannitol Powder | 75.000 |
| 5.000% | 85% Maltitol Syrup | 75.000 |
| 38.151% | Sorbitol Powder | 572.265 |
| 5.000% | Glycerin | 75.000 |
| 0.750% | Peppermint/Menthol Flavor Oil | 11.250 |
| 0.075% | Flavor Enhancer | 1.125 |
| 0.100% | Aspartame | 1.500 |
| 0.100% | Acesulfame K | 1.500 |

TABLE 2-continued

Experimental No. 1
Control Plus Essential Oils

| % of Formulation | Ingredient | Batch Quantity gms |
|---|---|---|
| 0.750% | Lecithin | 11.250 |
| 0.000% | Calcium carbonate (1–40 microns) | 0.000 |
| 0.000% | Sodium bicarbonate Powder | 0.00 |
| 0.000% | Citric Acid (encapsulated) | 0.00 |
| 0.020% | Eucalyptus Oil | 0.300 |
| 0.20% | Parsley Seed Oil | 0.300 |
| 0.017% | Thyme Oil | 0.255 |
| 0.17% | Myrrh Oil | 0.255 |

In this experiment the amount of sorbitol powder was decreased over the Control (Example I) and the essential oils, eucalyptus and thyme were increased while the essential oils myrrh and parsley were added. These changes were found to enhance the aromatic sensory characteristics of this product.

EXAMPLE III

The following Table 3 lists the compounds and amounts mixed in a 5 liter Stephan mixer to produce Experimental No. 2. The 1.5 kg batch was divided in 3.5 gm pieces after production and subjected to sensory evaluation.

TABLE 3

Experimental No. 2
Control Plus Increased Essential Oils Plus Calcium Carbonate and a
Two Fold Increase in Essential Oil Concentrations

| % of Formulation | Ingredient | Batch Quantity gms |
|---|---|---|
| 30.000% | Gum Base | 450.000 |
| 15.000% | Xylitol Powder | 225.000 |
| 5.000% | Mannitol Powder | 75.000 |
| 5.000% | 85% Maltitol Syrup | 75.000 |
| 33.097% | Sorbitol Powder | 496.455 |
| 5.000% | Glycerin | 75.000 |
| 0.750% | Peppermint/Menthol Flavor Oil. | 11.250 |
| 0.075% | Flavor Enhancer | 1.125 |
| 0.100% | Aspartame | 1.500 |
| 0.100% | Acesulfame K | 1.500 |
| 0.750% | Lecithin | 11.250 |
| 5.000% | Calcium carbonate (1–40 microns) | 75.000 |
| 0.000% | Sodium bicarbonate Powder | 0.00 |
| 0.000% | Citric Acid (encapsulated) | 0.00 |
| 0.040% | Eucalyptus Oil | 0.600 |
| 0.020% | Parsley Seed Oil | 0.300 |
| 0.034% | Thyme Oil | 0.510 |
| 0.034% | Myrrh Oil | 0.510 |

The product of this experiment was evaluated for organoleptic properties and was found adequate in sweetness. The increase in the calcium carbonate content had little effect on mouthfeel and taste. The essential oils, eucalyptus, thyme and myrrh were increased to further enhance the aromatic sensory characteristics of this product.

EXAMPLE IV

In this experiment the base gum stock (all components listed in Table 4 except the encapsulated citric acid) was prepared, rolled and cut into about 3.5 gm pieces. Each piece was then rolled in the encapsulated citric acid. This technique is known in the confection industry as "sanding".

TABLE 4

Experimental No. 3
Control Plus Increased Essential Oils Plus Calcium Carbonate and a Two Fold Increase in Essential Oil Concentrations Plus Sodium Bicarbonate Coated with Encapsulated Citric Acid in a Simulated Pan Coating

| % of Formulation | Ingredient | Batch Quantity gms |
|---|---|---|
| 30.000% | Gum Base | 450.000 |
| 15.000% | Xylitol Powder | 225.000 |
| 5.000% | Mannitol Powder | 75.000 |
| 5.000% | 85% Maltitol Syrup | 75.000 |
| 13.097% | Sorbitol Powder | 170.45 |
| 5.000% | Glycerin | 75.000 |
| 0.750% | Peppermint/Menthol Flavor Oil | 11.250 |
| 0.075% | Flavor Enhancer | 1.125 |
| 0.100% | Aspartame | 1.500 |
| 0.100% | Acesulfame K | 1.500 |
| 0.750% | Lecithin | 11.250 |
| 5.000% | Calcium carbonate (1–40 microns) | 75.000 |
| 11.364% | Sodium bicarbonate Powder | 170.45 |
| 8.636% | Citric Acid (encapsulated) | 129.55 (sanded) |
| 0.040% | Eucalyptus Oil | 0.600 |
| 0.020% | Parsley Seed Oil | 0.300 |
| 0.034% | Thyme Oil | 0.510 |
| 0.034% | Myrrh Oil | 0.510 |

The sensory tests indicated that the chewing gum effervested upon mastication, produced a pleasing sensation and taste, and left the teeth and gingiva feeling clean and stimulated.

EXAMPLE V

The following Table 5 lists the compounds and amounts mixed in a 5 liter Stephan mixer to produce Experimental No. 4.

TABLE 5

Experimental No. 4
Control Plus Increased Essential Oils Plus Calcium Carbonate and a Two Fold Increase in Essential Oil Concentrations Plus Sodium Bicarbonate Mixed with Encapsulated Citric Acid

| % of Formulation | Ingredient | Batch Quantity gms |
|---|---|---|
| 30.000% | Gum Base | 450.000 |
| 15.000% | Xylitol Powder | 225.000 |
| 5.000% | Mannitol Powder | 75.000 |
| 5.000% | 85% Maltitol Syrup | 75.000 |
| 13.097% | Sorbitol Powder | 196.455 |
| 5.000% | Glycerin | 75.000 |
| 0.750% | Peppermint/Menthol Flavor Oil | 11.250 |
| 0.075% | Flavor Enhancer | 1.125 |
| 0.100% | Aspartame | 1.500 |
| 0.100% | Acesulfame K | 1.500 |
| 0.750% | Lecithin | 11.250 |
| 5.000% | Calcium carbonate (1–40 microns) | 75.000 |
| 11.364% | Sodium bicarbonate Powder | 170.45 |
| 8.636% | Citric Acid (encapsulated) | 129.55 (mixed in) |
| 0.040% | Eucalyptus Oil | 0.600 |
| 0.020% | Parsley Seed Oil | 0.300 |
| 0.034% | Thyme Oil | 0.510 |
| 0.034% | Myrrh Oil | 0.510 |

From a taste testing panel it was determined that this formulation was not as tart as the product produced in Example 4, and that the flavor and essential oil levels should be increased. It was also determined that the effervescence, upon mastication, was not as prolonged when compared to Experimental No. 3. The effervescence reaction actually began to occur during processing in this experiment. This was considered unacceptable as this product would have no shelf-life. This Experiment demonstrated to the inventors that the acid component of the effervescent couple should be an outside coating of the base containing gum base stock. The results from these experiments demonstrate that a convenient and low cost chewing gum can be produced that has favorable organoleptic properties and a refreshing effervescent character.

EXAMPLE VI

From the information and experience gained in Examples I–V the inventors conducted a 3 kg. pilot scale production run of the inventive chewing gum formulation. Table 6 sets forth the list of ingredients, the percent of formulation and the quantity of each ingredient.

TABLE 6

| % of Formulation | Ingredient | Batch Quantity gms |
|---|---|---|
| 30.000% | Gum Base | 900 |
| 15.000% | Xylitol Powder | 450 |
| 5.000% | Mannitol Powder | 150 |
| 15.534% | Sorbitol Powder | 466.02 |
| 5.000% | Glycerin | 150 |
| 1.5% | Peppermint/Menthol Flavor Oil | 45 |
| 0.15% | Flavor Enhancer | 4.5 |
| 0.100% | Aspartame | 3.0 |
| 0.100% | Acesulfame K | 3.0 |
| 0.750% | Lecithin (soy bean) | 22.5 |
| 1.666% | Encapsulating Material from Citric Acid | 49.98 |
| 5.000% | Calcium carbonate (1–40 microns) | 150 |
| 10.559% | Sodium bicarbonate Powder | 316.77 |
| 11.107% | Citric Acid (encapsulated) | 283.23 |
| 0.060% | Eucalyptus Oil | 1.8 |

TABLE 6-continued

| % of Formulation | Ingredient | Batch Quantity gms |
|---|---|---|
| 0.020% | Parsley Seed Oil | 0.6 |
| 0.064% | Thyme Oil | 1.8 |
| 0.06% | Myrrh Oil | 1.8 |

Total batch size was 3.0 kg.

The gum base formulation was prepared by first dry blending the xylitol, mannitol and sorbitol to produce Dry Blend No. 1. The aspartame, acesulfame K, flavor enhancer and 5% of Dry Blend No. 1 were dry blended to prepare Dry Blend No. 2. The calcium carbonate and the sodium bicarbonate were dry blended to prepare Dry Blend No. 3. To a mixer (Sigma Blade) at 135° F. was added the gum base and the lecithin. Then one third of Dry Blend No. 1 was added to the mixer and mixing continued for about 2 minutes. Then about one third of Dry Blend No. 1 was added with all of Dry Blend No. 2 and mixing continued for about 3 minutes, after which the remaining third of Dry Blend No. 1 was added and mixing continued for about 3 minutes. About one half of Dry Blend No. 3 was added and after about 2 minutes of mixing one half of the glycerin was added and the remaining one half of Dry Blend No. 3. After about 3 minutes of mixing the remaining one half of the glycerin was added and mixing continued for another 3 minutes, after which all of the oils were added and mixing continued for about 2 minutes. The product was then dumped onto wax paper and rolled into sheets. After cooling, the gum base formulation was cut into 1.5 gm pieces and tempered overnight prior to coating.

The coating containing the edible acid was applied to the gum base formulation pieces through the use of a Pan Coating machine. The gum pieces were added to the Pan and 10 gms of a 25% total solids solution of gum arabic in water was then slowly added to thoroughly wet the pieces. 88.28 gms of sorbitol powder was then added slowly as the gum pieces sweat back moisture. More gum arabic solution was added as the pieces became too dry to pick up more sorbitol. After addition of all the sorbitol, the pieces were tumbled until dry. A powder mixture of 34.33 gms of sorbitol and 111.07 gms of the encapsulated citric acid was then prepared. After re-wetting the pieces with the gum arabic solution, the sorbitol/citric acid powder was slowly added. A final hard coat was then added which consisted of 74.11 gms of 70% total solid solution of sorbitol and 8.00 gms of $TiO_2$.

EXAMPLE VII

Using the procedure described in Example VI, yet another effervescent chewing gum according to the invention was prepared. The amount of each ingredient used is set forth in Table 7.

TABLE 7

| % of Formulation | Ingredient | Batch Quantity gms |
|---|---|---|
| 30.000% | Gum Base | 900 |
| 15.000% | Xylitol Powder | 450 |
| 5.000% | Mannitol Powder | 150 |
| 0.15% | Powdered Mint Flavor | 4.5 |
| 15.114% | Sorbitol Powder | 453.42 |
| 5.000% | Glycerin | 150 |

TABLE 7-continued

| % of Formulation | Ingredient | Batch Quantity gms |
|---|---|---|
| 1.5% | Peppermint/ Menthol Flavor Oil | 45 |
| 0.3% | Flavor Enhancer | 9.0 |
| 0.32% | Acesulfame K | 9.6 |
| 0.750% | Lecithin (soy bean) | 22.5 |
| 1.666% | Encapsulating Material | 49.98 |
| 5.000% | Calcium carbonate (1–40 microns) | 150 |
| 10.559% | Sodium bicarbonate Powder | 316.77 |
| 11.107% | Citric Acid (encapsulated) | 283.23 |
| 0.060% | Eucalyptus Oil | 1.8 |
| 0.020% | Parsley Seed Oil | 0.6 |
| 0.06% | Thyme Oil | 1.8 |
| 0.06% | Myrrh Oil | 1.8 |

In a manner similar to that described in Example VI the gum pieces were prepared and the coating was applied. In this formulation the sweetness and flavor intensity were increased over the formulation of Example VI.

EXAMPLE VIII

In an effort to increase the effervescence, yet another chewing gum according to the invention was prepared in this Example. The listing of ingredients is set forth in Table 8.

TABLE 8

| % of Formulation | Ingredient | Batch Quantity gms |
|---|---|---|
| 30.000% | Gum Base | 900 |
| 15.000% | Xylitol Powder | 450 |
| 5.000% | Mannitol Powder | 150 |
| 0.150% | Powdered Mint Flavor | 4.5 |
| 15.114% | Sorbitol Powder | 453.42 |
| 5.000% | Glycerin | 150 |
| 1.5% | Peppermint/ Menthol Flavor Oil | 45 |
| 0.3% | Flavor Enhancer | 9.0 |
| 0.32% | Acesulfame K | 9.6 |
| 0.750% | Lecithin (soy bean) | 22.5 |
| 1.666% | Encapsulating Material | 49.98 |
| 5.000% | Calcium carbonate (1–40 microns) | 150 |
| 10.559% | Sodium bicarbonate Powder | 316.77 |
| 11.107% | Citric Acid (encapsulated) | 283.23 |
| 0.060% | Eucalyptus Oil | 1.8 |
| 0.020% | Parsley Seed Oil | 0.6 |
| 0.06% | Thyme Oil | 1.8 |
| 0.06% | Myrrh Oil | 1.8 |

EXAMPLE IX

A consumer panel was organized and evaluated the oral maintenance chewing gums prepared in Examples VI–VIII. The panel was requested to rank the following: tartness, foaming/effervescence, long lasting flavor, chewing properties, and overall mouthful. Characteristics were reported as Very Bad, Bad, OK, Good and Very Good using a scale of 1 for Very Bad and 5 for Very Good.

The results of this sensory panel are shown in Table 9.

TABLE 9

Sensory Evaluation *

|  | Exp. VI<br>n = 19 | Exp. VII<br>n = 31 | Exp. VIII<br>n = 26 |
| --- | --- | --- | --- |
| Tartness | 2.58 | 2.81 | 2.35 |
| Foaming/Effervescence | 4.00 | 3.40 | 3.54 |
| Long Lasting Flavor | 3.21 | 3.52 | 3.52 |
| Chewing Properties | 3.74 | 4.03 | 3.69 |
| Overall Mouthfeel | 3.42 | 3.90 | 3.62 |
| Product Claims** | 3.76 | 3.69 | 3.84 |

* reported as average of value from consumer
**initial blast of tartness to induce salivary flow, effervescence, long lasting cool minty flavor to freshen breath As set forth in Table 9 the consumers overall found the chewing gums according to the invention to provide a pleasant experience. In general the chewing gum produced in Example VII was favored over the gums produced in Examples VI and VIII.

EXAMPLE X pH of Gum

To test the changing pH of Experimental No. VII one piece of the gum produced in Example VII was ground and diluted (50%) with dionized water. The initial pH registered 3.62 then the pH slowly climbed over a period of 2.5 hours to final stabilized pH of 7.82. Of course the pH change in the mouth of a human would be much more rapid as the chewing would facilitate the mixing of the ingredients.

EXAMPLE XI pH of Gum

An 8.3 gm sample of the chewing gum produced in Example VIII was diluted with distilled water (1:1). The sample was stirred and the pH checked at 15 minute intervals. The initial pH at 25° C. was 3.49. The pH steadily increased over a five hour period while dissolving. The final pH was 7.64.

From Examples X and XI it is evident that the chewing gums according to the invention perform as designed, that is, the product is initially acidic but eventually becomes basic. This is a function of the acid to base ratio. The chewing gums according to the invention will provide a final pH of 6.0 or above to help neutralize the acids generated by byproducts of the fermentation of food particles by oral bacteria. It is these acids that lead to the development of plaque.

Industrial Applicability

Adhesion of oral bacteria to surfaces in the oral cavity is one of the main events leading to oral diseases and halitosis. The formation of dental plaque leads to tooth decay, calculus and gingivitis. Mechanical removal (i.e. brushing and flossing) of the plaque is still the best method and the chewing gum, according to this invention, is designed to promote plaque removal and reduce the adhesion of oral bacteria to the oral cavity. As chewing gum is popular among adults and young people, the product, according to this invention, would benefit the overall population in reducing oral disease. The inventive chewing gum with its unique combination of an edible acid in the coating, which stimulates the salivary glands, and effervescent properties combined with selected flavor oils, polishing and whitening agents, results in a unique experience. In a preferred embodiment of the invention, the chewing gum is sugar free and utilizes xylitol as a sweetening agent. Xylitol does not promote tooth decay. Thus, the chewing gum, according to the invention, will thus reduce plaque and freshen the breath without side effects (i.e. change in beneficial oral microflora). The chewing gum in a preferred embodiment not only provides a pleasing effervescence but also good flavor, texture and mouthfeel without offensive abrasiveness.

While the formula and method of making said effervescent chewing gum disclosed herein constitute a preferred embodiment of this invention, it is to be understood that the invention is not limited to this precise formulation or method and that changes may be made therein without departing from the scope of the invention which is defined in the appended claims.

What is claimed is:

1. A solid chewable piece of chewing gum comprising:
   a) a chewing gum base wherein said base comprises at least one component selected from the group consisting of alkali metal carbonates, alkali metal bicarbonates, alkaline earth metal carbonates, alkaline earth metal bicarbonates and mixtures thereof; and
   b) a coating covering said base wherein said coating comprises at least one encapsulated edible acid selected from the group consisting of tartaric acid, citric acid, malic acid, ascorbic acid, acid phosphate salts, and mixtures thereof;
   said at least one component in said base and said at least one edible acid in said coating being in the range of from about 10 to about 50 percent by weight of said chewing gum;
   wherein said at least one component in said base is adapted to react with said at least one edible acid during chewing of said chewing gum to produce effervescence.

2. The chewing gum according to claim 1 wherein said gum base comprises at least one additional component selected from the group consisting of sweeteners, therapeutic agents, flavoring agents, processing aids, edible oils and breath fresheners.

3. The chewing gum according to claim 1 wherein the concentration of said at least one component in said base and said at least one edible acid in said coating is in the range of from about 20 to about 35 percent by weight of said chewing gum.

4. The chewing gum according to claim 1 wherein:
   said mixtures thereof in said base are present in an amount of about 5 to about 25 percent by weight of said gum; and
   said at least one edible acid in said coating is present in an amount of about 5 to about 15 percent by weight of said gum.

5. The chewing gum according to claim 1 wherein said at least one component in said base is sodium bicarbonate.

6. The chewing gum according to claim 1 wherein said at least one component in said base is sodium bicarbonate and calcium carbonate.

7. The chewing gum according to claim 1 wherein the weight ratio of said at least one edible acid to said at least one component in said base is between about 0.5 and about 2.0.

8. The chewing gum of claim 1 wherein the pH of said chewing gum during initial chewing of said gum is less than about 4.0 and upon further chewing of said chewing gum is at least about 7.0.

9. The chewing gum of claim 8 wherein the weight ratio of said at least one edible acid in said coating to said at least one component in said base is between about 0.5 and about 2.0.

10. A sugar-free, effervescent chewing gum comprising:
1) a base formulation comprising:
   a) sodium bicarbonate,
   b) xylitol,
   c) at least one artificial sweetener,
   d) at least one oil selected from the group consisting of: parsley seed oil, eucalyptus oil, thyme oil and myrrh oil; and
2) a coating formulation comprising an encapsulated edible acid, said edible acid adapted to react with said sodium bicarbonate during chewing of said chewing gum to produce effervescence, said edible acid selected from the group consisting of tartaric acid, citric acid, malic acid, ascorbic acid, acid phosphate salts, and mixtures thereof;
wherein said sodium bicarbonate in said base and said edible acid in said coating are in the range of from about 10 to about 50 percent by weight of said chewing gum.

11. The chewing gum according to claim 10 wherein said base formulation additionally comprises at least one component selected from the group consisting of calcium carbonate, lecithin, glycerin, natural flavors, artificial flavors, coloring agents and acesulfame K.

12. The chewing gum according to claim 11 wherein said base comprises sodium bicarbonate and calcium carbonate.

13. The chewing gum according to claim 12 wherein the weight ratio of said edible acid to said sodium bicarbonate and said calcium carbonate ranges from about 0.6 to about 1.0.

14. The chewing gum according to claim 10 wherein said oil is a mixture of parsley seed oil, eucalyptus oil, thyme oil and myrrh oil.

15. The chewing gum according to claim 10 wherein said base formulation additionally comprises calcium carbonate and the weight ratio of said acid to said sodium bicarbonate is 0.6 to 1.0.

16. The chewing gum according to claim 10 wherein the concentration of said sodium bicarbonate and said edible acid is in the range of from about 20 to about 35 percent by weight of said chewing gum.

17. The chewing gum of claim 10 wherein the pH of said chewing gum during initial chewing of said gum is less than about 4.0 and upon further chewing of said chewing gum is at least about 7.0.

18. The chewing gum of claim 17 wherein the weight ratio of said edible acid in said coating to said sodium bicarbonate in said base is between about 0.5 and about 2.0.

19. An effervescent solid piece of chewing gum having a coating, said piece of chewing gum comprising by weight:
   a) 25–35% gum base;
   b) 30–40% of at least one compound selected from xylitol, mannitol and sorbitol;
   c) 2–10% glycerin;
   d) 0.1–0.5% of at least one oil selected from peppermint, menthol, eucalyptus, parsley, thyme and myrrh;
   e) 0.2–0.5% of at least one artificial sweetener;
   f) 0.5–1.0% lecithin;
   g) 2.0–10% calcium carbonate;
   h) 5.0–15% sodium bicarbonate; and
   i) 5.0–15% of at least one edible acid, said at least one edible acid being encapsulated and included in said coating of said piece of chewing gum;
wherein said sodium bicarbonate is adapted to react with said at least one edible acid during chewing of said chewing gum to produce effervescence.

20. The chewing gum of claim 19 wherein the pH of said chewing gum during initial chewing of said gum is less than about 4.0 and upon further chewing of said chewing gum is at least about 7.0.

* * * * *